(12) United States Patent
Bongers et al.

(10) Patent No.: US 12,325,886 B2
(45) Date of Patent: Jun. 10, 2025

(54) DRYING OF ALLULOSE CRYSTALS

(71) Applicant: SAVANNA INGREDIENTS GMBH, Elsdorf (DE)

(72) Inventors: Ulrich Bongers, Kerpen (DE); Stephan Mohr, Euskirchen (DE); Steffen Butz, Kreuzau (DE); Anna Junklewitz, Wuppertal (DE); Timo Koch, Elsdorf (DE); Michael Bognar, Dormagen (DE)

(73) Assignee: SAVANNA INGREDIENTS GMBH, Elsdorf (DE)

( * ) Notice: Subject to any disclaimer, the term of this patent is extended or adjusted under 35 U.S.C. 154(b) by 0 days.

(21) Appl. No.: 18/220,603

(22) Filed: Jul. 11, 2023

(65) Prior Publication Data

US 2023/0349013 A1    Nov. 2, 2023

Related U.S. Application Data

(63) Continuation of application No. 17/529,841, filed on Nov. 18, 2021, now Pat. No. 11,746,392.

(30) Foreign Application Priority Data

Nov. 23, 2020    (EP) ..................... 20209177

(51) Int. Cl.
C13K 13/00    (2006.01)
(52) U.S. Cl.
CPC ................... C13K 13/00 (2013.01)
(58) Field of Classification Search
CPC . C13K 13/00; C07H 1/00; C07H 1/06; C07H 3/02; A23L 27/33; A23L 3/40; A23L 3/48; A23L 3/50; A23V 2002/00; A23V 2300/10; A23V 2300/24
USPC .......................................................... 127/30
See application file for complete search history.

(56) References Cited

U.S. PATENT DOCUMENTS

| | | | |
|---|---|---|---|
| 3,880,593 A | 4/1975 | Windal | |
| 4,357,172 A | 11/1982 | Edwards | |
| 5,411,880 A | 5/1995 | Izumori et al. | |
| 8,030,035 B2 | 10/2011 | Oh et al. | |
| 8,735,106 B2 | 5/2014 | Hong et al. | |
| 2011/0237790 A1 | 9/2011 | Lee et al. | |
| 2014/0342044 A1 | 11/2014 | Bell et al. | |
| 2014/0370171 A1 | 12/2014 | Takaoka et al. | |
| 2015/0210996 A1 | 7/2015 | Woodyer et al. | |
| 2016/0050954 A1 | 2/2016 | Barre et al. | |
| 2016/0302463 A1 | 10/2016 | Woodyer et al. | |
| 2017/0064988 A1 | 3/2017 | Prakash et al. | |
| 2017/0313734 A1 | 11/2017 | Kim et al. | |
| 2018/0049458 A1 | 2/2018 | Woodyer et al. | |
| 2018/0255814 A1 | 9/2018 | Park et al. | |
| 2018/0271112 A1 | 9/2018 | Barkalow et al. | |
| 2018/0271113 A1 | 9/2018 | Parady et al. | |
| 2018/0279643 A1 | 10/2018 | Barkalow et al. | |
| 2018/0281263 A1 | 10/2018 | Rust | |
| 2018/0327796 A1 | 11/2018 | Lee et al. | |
| 2019/0029299 A1 | 1/2019 | Bak et al. | |
| 2019/0090528 A1 | 3/2019 | Boit et al. | |
| 2019/0232720 A1 | 8/2019 | Prost et al. | |
| 2019/0246673 A1 | 8/2019 | Park et al. | |
| 2019/0297931 A1 | 10/2019 | Koch et al. | |
| 2019/0330253 A1 | 10/2019 | Boit et al. | |
| 2020/0001502 A1 | 1/2020 | Rust | |
| 2020/0040023 A1 | 2/2020 | Iyer et al. | |
| 2020/0062792 A1 | 2/2020 | Dou et al. | |
| 2020/0085090 A1 | 3/2020 | Boit et al. | |
| 2020/0196648 A1 | 6/2020 | Kim et al. | |
| 2020/0385415 A1 | 12/2020 | Park et al. | |
| 2021/0009619 A1 | 1/2021 | Iyer et al. | |

FOREIGN PATENT DOCUMENTS

| | | |
|---|---|---|
| CN | 101109021 A | 1/2008 |
| CN | 104447888 A | 3/2015 |
| CN | 107699557 A | 2/2016 |
| CN | 106480125 A | 3/2017 |
| CN | 109306365 A | 2/2019 |
| CN | 110627847 A | 12/2019 |
| CN | 110 872 332 A | 3/2020 |
| DE | 2315835 B2 | 10/1973 |
| EP | 0919127 A1 | 6/1999 |
| EP | 2552241 A2 | 2/2013 |
| EP | 3553071 A1 | 10/2019 |

(Continued)

OTHER PUBLICATIONS

Kweicien et al., Crystal Structure of β-D-psicopyranose, 2008, Carbohydrate Research, 343, 2236-2239 (Year: 2008).*
Lakanto: What's Allulose? [online], [retrieved Mar. 23, 2024]. Retrieved from the Internet < URL:https://www.lakanto.com/pages/all-about-allulose-sweetener#:~:text=Allulose%20is%20a%20type%20of,ability%20to%20caramelize%20and%20brown.> (Year: 2024).*
A. Kwiecien et al., "Crystal Structure of ß-D-psicopyranose", Carbohydrate Research, 343(13), 2008, 2336-2339.
K. Fukada et al., "Crystal Structure, Solubility, and Mutarotation of the Rare Monosaccharide D-Psicose", Bulletin of the Chemical Society of Japan, 2010, 83(10), 1193-1197.

(Continued)

*Primary Examiner* — Colin W. Slifka
(74) *Attorney, Agent, or Firm* — The Dobrusin Law Firm, P.C.

(57) ABSTRACT

The teachings herein relate to a process for drying allulose crystals. The process includes a step of providing non-dried allulose crystals. The process includes temperature treating the crystals at a temperature in the range of about 25 to about 70° C. in a drying apparatus to form an intermediate product. The process includes conditioning the intermediate process. The conditioning may be for about 30 minutes to 7 hours at 40 to 70° C. The conditioning may be for about 15 to about 90 hours with air of a relative humidity of about 30 to about 60% at 25 to about 40° C.

20 Claims, No Drawings

(56) References Cited

FOREIGN PATENT DOCUMENTS

| | | | |
|---|---|---|---|
| GB | 2536304 | A | 9/2016 |
| JP | H05277000 | A | 10/1993 |
| JP | 2005006520 | A | 1/2005 |
| KR | 20160062349 | A | 6/2016 |
| KR | 2019/0003307 | A | 1/2019 |
| KR | 10-2020-001831 | A | 2/2020 |
| WO | 2015/075473 | A1 | 5/2015 |
| WO | 2016/012854 | A1 | 1/2016 |
| WO | 2016/135358 | A1 | 9/2016 |
| WO | 2016/135458 | A1 | 9/2016 |
| WO | 2017/029244 | A1 | 2/2017 |
| WO | 2018/087261 | A1 | 5/2018 |
| WO | 2018/105931 | A1 | 6/2018 |
| WO | 2018/149707 | A1 | 8/2018 |
| WO | 2019/004554 | A1 | 1/2019 |
| WO | 2019/082206 | A1 | 5/2019 |
| WO | 2019/083069 | A1 | 5/2019 |
| WO | 2019/088654 | A1 | 5/2019 |
| WO | 2020/005021 | A1 | 1/2020 |
| WO | 2021/160564 | A1 | 8/2021 |
| WO | 2021/239813 | A1 | 12/2021 |

OTHER PUBLICATIONS

J. Angyal et al., "The Composition of Reducing Sugars in Solution", Advances in Carbohydrate Chemistry, vol. 42, Academic Press, New York, 1984, 15-68.
R.N. Goldberg et al., "Thermodynamic and Transport Properties of Carbohydrates and their Monophophates: The Pentoses and Hexoses", Journal of Physical and Chemical Reference Data, vol. 18(2), 1989, 809-880, p. 827.
American Society of Agricultural and Biological Engineers (ASABE), ANSI/ASAE S319.4 Feb. 2008 "*Method of Determining and Expressing Fineness of Feed Materials by Sieving*".
Sugar Technology, Beet and Cane Sugar Manufacture, Peter van der Poel, Hubert Schiweck, Tom Schwartz, 1998. Chapters 12-14. (particularly chapter 14).
European Search Report, EP Application No. 20209177.3 dated Apr. 7, 2021; Corresponding Patent Application with the European Patent Office (translation not available).
H. Itoh, et al., "Preparation of D-Psicose from D-Fructose by Immobilized D-Tagatose 3-Epimerase", Journal of Fermentation Bioengineering, 80(1), pp. 101-103 (1995).
N. Wagner, et al., "Practical Aspects of Integrated Operation of Biotransformation and SMB Separation for Fine Chemical Synthesis", Organic Process Research Development, 16, pp. 323-330 (2012).
N. Wagner, et al., "Model-based cost optimization of a reaction-separation integrated process for the enzymatic production of rare sugar D-psicose at elevated temperatures", Chemical Engineering Science, 137, pp. 423-435 (2015).
N. Wagner, et al., "A Separation-Integrated Cascade Reaction to Overcome Thermodynamic Limitations in Rare-Sugar Synthesis", Angewandte Chemie [Applied Chemistry] Int. Ed. Engl. 54(14), pp. 4182-4186 (2015).
Bosshart, et al., "Highly Efficient Proeduction of Rare Sugars D-Psicose and L-Tagatose by Two Engineered D-Tagatose Epimerases", Biotechnology Bioengineering, 113(2), pp. 349-358 (2016).
N. Wagner, et al., "Multi-objective optimization for the economic production of D-psicose using simulated moving bed chromatography", Journal of Chromatography A, 1398, pp. 47-56, (2015).
Richardson, Hygroscopicity, retrieved from the internet: http://www.thermopedia.com/content/869/ (2011).
Office Action, U.S. Appl. No. 18/220,605 dated Apr. 5, 2024.

* cited by examiner

DRYING OF ALLULOSE CRYSTALS

FIELD OF THE INVENTION

The invention is in the field of food technology and relates to a process for drying allulose crystals.

TECHNOLOGICAL BACKGROUND

Allulose (Psicose) is a low-calorie sugar with similar sweet taste of sugar. Allulose is one of many different sugars found in nature in very small amounts. Allulose was originally identified from wheat and has since been found in certain fruits such as jackfruit, figs and raisins. Allulose is naturally found in small amounts in a variety of sweet foods such as caramel sauce, maple syrup and brown sugar. Allulose is absorbed but not metabolized by the body, making it virtually calorie-free.

Due to the growing interest of a large portion of the population in "healthy eating" and "healthy living" in general, allulose has attracted a great deal of interest in the food industry and scientific community as a calorie-free sugar.

Allulose is often commercialized in the form of crystals.

RELEVANT STATE OF THE ART

Processes for the preparation of allulose in crystalline form are known in the prior art. For example, document EP 2 552 241 B1 (CJ CHEILJEDANG CORP) discloses a process for producing D-psicose comprising the following steps: (a) removing impurities from a D-psicose solution to obtain a purified D-psicose solution, (b) concentrating the purified D-psicose solution at a temperature of 60° C. to 70° C., and (c) crystallizing the D-psicose from the concentrated D-psicose solution in a supersaturated state under a metastable zone. The process comprises recovering the D-psicose crystals obtained during crystallization, and washing the crystals with deionized water and drying the crystals. Drying of the crystals can be performed in a fluidized bed dryer or a vacuum dryer.

However, producers of allulose in crystalline form are faced with the problem that the dried allulose crystals reabsorb moisture very quickly, depending on the drying method. This hygroscopicity of dried allulose crystals causes not only difficulties in handling, but also a reduction in the storage stability of the product.

Therefore, there is a strong need in the field of food technology for energy-saving processes that allow improved drying of high-quality allulose crystals.

TASK OF THE INVENTION

The task of the present invention has thus been to provide a process for drying allulose crystals which are free from the disadvantages described at the outset. In particular, the allulose crystals obtained should have a low hygroscopicity.

Thus, a second object of the present invention has been to provide a method for drying allulose crystals such that the obtained allulose crystals are free-flowing, readily soluble in water and have a good taste.

DESCRIPTION OF THE INVENTION

It is an object of the present invention to provide a process for drying allulose crystals comprising or consisting of the following steps:

(a) providing non-dried allulose crystals,
(b) temperature-treating the crystals according to step (a) at a temperature in the range of about 25 to about 70° C. in a drying apparatus, wherein the temperature treatment is carried out
   (b1) at atmospheric pressure and a residence time in the range of about 5 minutes to about 5 hours, or
   (b2) under reduced pressure and constant temperature and a residence time ranging from about 30 min to 5 hours, and
(c) conditioning the intermediate product obtained in step (b1) or (b2), wherein conditioning is carried out
   (c1) over a period of about 30 min to 7 hours at a temperature in the range of about 40 to about 70° C., or
   (c2) over a period of about 15 to 90 hours with air of a relative humidity of about 30 to about 60% and at a temperature of about 25 to about 40° C.

Surprisingly, it was found that allulose crystals dried by the method of the invention present a free-flowing product, and have a considerably lower hygroscopicity than allulose crystals dried by the standard conditions. Accordingly, the obtained allulose crystals are characterized by considerable storage stability.

Furthermore, it was surprisingly found that allulose crystals dried by means of the process according to the invention are in particular easily soluble and sensorially perfect.

Allulose, also known as psicose, is a ketohexose. For the purposes of the present invention, allulose is preferably provided in the form of the D-enantiomer, i.e. D-allulose (CAS No. 551-68-8). D-allulose may be in the form of various anomers such as α-D-allulose and β-D-allulose.

For the purposes of the present invention, the term "temperature treatment" of step (b) should also be understood as "drying" or "tempering."

For the purposes of the present invention, the term "conditioning" is also to be understood as a "post-crystallization" which is carried out in the absence of a solvent. That is, the intermediates obtained in steps (b1) or (b2) are not brought into contact with a solvent during step (c).

In terms of the present invention, the process used to produce the non-dried allulose crystals according to step (a) is not critical for the successful performance of the drying process according to the invention.

However, in a preferred embodiment, the non-dried allulose crystals according to step (a) have a purity greater than 95%, preferably greater than 98%, and more preferably in the range of 98.5 to 99.5%—in each case based on the total dry mass.

In a preferred embodiment of the drying process according to the invention, at least 10% by weight, at least 20% by weight, at least 30% by weight, at least 40% by weight, at least 50% by weight, at least 60% by weight, at least 70% by weight, at least 80% by weight, at least 90% by weight, at least 95% by weight, or at least 98% by weight, at least 99 wt. % of the allulose in the non-dried allulose crystals of step (a) is present in the form of β-D-psicopyranose—in each case again based on the total dry weight.

In the sense of the present invention, the non-dried allulose crystals of step (a) are obtained from a concentrated allulose suspension by means of separation, in particular by means of centrifugation or filtration, from the mother liquor.

In a preferred embodiment, the non-dried allulose crystals according to step (a) have a water content of at most about 40% by weight at most, preferably of about 35% by weight at most, preferably of about 30% by weight at most, preferably of about 25% by weight at most, preferably of about 20% by weight at most, preferably of about 15% by weight at most, preferably of about 10% by weight at most, preferably of about 9% by weight at most, preferably of about 8% by weight at most. %, preferably of at most about 7% by weight, preferably of at most about 6% by weight, preferably of at most about 5% by weight, preferably of at most about 4% by weight, preferably of at most about 3% by weight, preferably of at most about 2% by weight, preferably of at most about 1% by weight, and preferably of at most about 0.5% by weight.

In another preferred embodiment, the non-dried allulose crystals according to step (a) have a water content of about 10-0.3 wt.-%, preferably of about 8-0.4 wt.-%, and more preferably of about 5-0.5 wt.-%.

As mentioned above, the non-dried allulose crystals according to step (a) are subjected to a temperature treatment in a drying plant. The temperature treatment according to step (b)—in both variant (b1) and variant (b2)—is carried out at a temperature in the range from about 25 to about 70° C.

In a preferred embodiment, the temperature treatment of step (b) is carried out at a temperature in the range from about 30 to about 65° C. and, in particular, preferably in the range from about 30 to about 60° C.

In terms of the present invention, various drying systems are suitable for carrying out the temperature treatment according to step (b), for example, drum dryers, belt dryers, shaft dryers, conical dryers, convection dryers, vibrating fluidized bed dryers, fluidized bed dryers, tube bundle dryers, thin layer dryers, disc dryers, vacuum dryers, contact dryers and microwave dryers. These drying systems are well known to those skilled in the art and therefore need not be explained in detail.

However, carrying out the temperature treatment according to step (b) in a drying plant selected from the group consisting of fluidized bed dryer (continuous), vacuum dryer, belt dryer and thin film dryer, in particular fluidized bed dryer and vacuum dryer, has proven to be particularly advantageous.

According to the invention, the temperature treatment can be carried out either by means of variant (b1) or by means of variant (b2).

As mentioned above, the temperature treatment according to (b1) is carried out at atmospheric pressure and a residence time in the drying system in the range of about 5 minutes to about 5 hours.

In a preferred embodiment, the temperature treatment according to (b1) is carried out at a constant temperature (which of course falls within the range defined in (b)).

In another preferred embodiment, the drying system in (b1) has different heating zones. The different heating zones are the individually controllable, so that it is possible to create an arbitrary temperature profile.

In a preferred embodiment, the drying system in (b1) has 2 to 5 different heating zones. Each heating zone has a different temperature, with the temperatures of each heating zone naturally falling within the range defined in (b); non-adjacent heating zones may have the same temperature. In a preferred embodiment, the dwell time per heating zone of the drying system is about 1 to about 8 minutes, preferably about 3 to about 8 minutes, more preferably about 4 to about 7 minutes.

It has been found to be particularly advantageous in terms of energy if the drying system has three different heating zones in step (b1). In a preferred embodiment, the temperature profile corresponds to the following scheme:

$$T1_{Heating\ zone} < T2_{Heating\ zone} > T3_{Heating\ zone}, \text{ where } T1_{Heating\ zone} \geq T3_{Heating\ zone}$$

or $$T1_{Heating\ zone} < T2_{Heating\ zone} > T3_{Heating\ zone}, \text{ where } T1_{Heating\ zone} \leq T3_{Heating\ zone}$$

In a preferred embodiment, the temperatures in the 3 different heating zones are set as follows:

$T1_{Heating\ zone}$ is in the range of 30-45° C., preferably, 35-40° C., and more preferably, 40° C.;

$T2_{Heating\ zone}$ is in the range of 50-70° C., preferably, 55-65° C., and more preferably 60° C.;

$T3_{Heating\ zone}$ is in the range of 25-35° C., preferably, 25-30° C., and more preferably 30° C.

In a preferred embodiment, if the drying system has three different heating zones, the residence time per heating zone of the drying system is about 3 to 8 minutes, preferably 4 to 6 minutes, and more preferably 4 minutes.

As mentioned above, the temperature treatment according to (b2) is carried out under reduced pressure and constant temperature (which of course falls within the range defined in (b)) and a residence time in the drying plant of about 30 min to 5 hours.

In a preferred embodiment, the temperature treatment according to step (b2) is carried out at a pressure of from about 5 to about 300 mbar, preferably from about 10 to about 250 mbar and particularly preferably at a pressure of from about 20 to about 200 mbar.

In a preferred embodiment, the temperature treatment according to step (b2) is carried out at a temperature in the range from about 25 to about 45° C., preferably from about 30 to about 40° C., and particularly preferably from about 30 to about 35° C.

In another preferred embodiment, the residence time in the drying system is from about 1 to about 4 hours, preferably from about 2 to about 4 hours, and more preferably about 3 hours.

In a particularly preferred embodiment, the temperature treatment according to step (b2) is carried out at a pressure of about 20 to about 200 mbar and a temperature of about 30 to about 40° C. and a residence time in the drying plant of about 3 hours.

The water content of the intermediate product obtained in step (b1) or (b2) is in the range of from about 0.1 to about 0.5 wt.-%, preferably from about 0.1 to about 0.3 wt.-%, more preferably from about 0.15 to about 0.25 wt.-%.

Although the intermediate product obtained in step (b1) or (b2) has a significantly reduced water content compared to the non-dried allulose crystals of step (a), the properties of this intermediate product are not satisfactory, especially with respect to the pourability of the product.

According to the invention, after the temperature treatment, conditioning of the intermediate product obtained in step (b1) or (b2) is carried out. By this is meant storing the intermediates obtained in step (b1) or (b2) for a certain period of time at a certain temperature or in contact with an air having specific properties with respect to water loading, so that a kind of "post-crystallization" takes place.

In the sense of the present invention, various devices for carrying out the conditioning according to step (c)—both in variant (c1) and in variant (c2)—can be considered, for example drum dryers, belt dryers, shaft dryer, conical dryer, convection dryer, vibrating fluidized bed dryer, fluidized bed dryer, tube bundle dryer, thin layer dryer, disc dryer, vacuum dryer, big bags, or conveyor system for pneumatic conveying (e.g., in a silo). These drying systems are well known to those skilled in the art and therefore need not be explained in detail.

In a preferred embodiment, the conditioning according to step (c) is carried out in a device selected from the group consisting of a drum dryer, fluid bed dryer, vacuum dryer, thin layer dryer, or a conveyor system for pneumatic conveying (e.g., in a silo).

In terms of the present invention, performing the conditioning does not necessarily require transferring the intermediate product according to (b1) or (b2) from a first apparatus where the temperature treatment was performed to a second apparatus where the conditioning is to be performed. It is quite possible to carry out steps (b) and (c) in their respective variants in the same device. For example, a temperature treatment according to (b2) can be performed in a vacuum dryer, and the conditioning can be performed in the same vacuum dryer.

In a first variant (c1), the conditioning is performed over a period of about 30 minutes to 7 hours at a temperature in the range of about 40 to about 70° C.

In a preferred embodiment, the conditioning according to (c1) is carried out at a temperature in the range of about 50 to about 70° C., preferably in the range of about 55 to about 65° C., more preferably in the range of about 58 to about 62° C.

In a further preferred embodiment, the conditioning according to (c1) is carried out over a period of about 30 minutes to 6 hours at a temperature>50° C.

In a very particular preferred embodiment, the conditioning according to (c1) is carried out over a period of time of about 3 to 6 hours at a temperature of about 60° C.

In variant (c2), the conditioning is carried out over a period of about 15 to about 90 hours with air of a relative humidity of about 30 to about 60% and at a temperature of about 25 to about 40° C.

In a preferred embodiment, the conditioning according to (c2) is carried out over a period of about 24 to about 72 hours and air to a temperature of about 30 to about 35° C., preferably 30° C.

In a further embodiment, the conditioning according to (c2) is carried out with air from a relative humidity of about 35 to about 55%, preferably from about 35 to about 45%, and particularly preferably about 40 to about 45%.

In a particularly preferred embodiment, the conditioning according to (c2) is carried out over a period of about 24 to about 72 hours and with air of a relative humidity of about 40% and to a temperature of about 30° C.

In another preferred embodiment, the conditioning according to (c2) is carried out in a thin film dryer, wherein the distributed intermediate product from the temperature treatment has a film thickness<10 mm.

The dried allulose crystals obtained by means of the process according to the invention have a water content of at most 0.1% by weight, preferably of at most 0.01% by weight, and particularly preferably of at most 0.001% by weight.

Accordingly, it is also an object of the present invention to provide allulose crystals having a content of water of at most 0.001% by weight, wherein the dried allulose crystals are produced by means of the process described above.

In summary, the process according to the invention allows obtaining high quality allulose crystals which are free-flowing and characterized by excellent solubility, low hygroscopicity and excellent sensory properties.

EXAMPLES

The present invention will be more readily understood with reference to the examples below.

However, these examples are merely illustrative of the invention and cannot be construed as limiting the scope of protection of the invention.

Comparative Example C1

Allulose crystals were obtained by centrifugation from the mother liquor from a concentrated allulose suspension (content of allulose in total dry matter of 97% by weight). The separated allulose crystals were then dried for 24 hours in a vacuum drying oven at 30° C. and a pressure of 10 mbar. A product was obtained which had a purity of 98% and a water content of 0.15 wt.-%. It was found that the product was highly hygroscopic and non-free-flowing.

Example 1 (According to the Invention)

Allulose crystals were obtained by centrifugation from the mother liquor from a concentrated allulose suspension (content of allulose in total dry matter of 97 wt.-%). The separated allulose crystals were subjected to temperature treatment in a continuous fluid bed dryer. The fluid bed dryer had three heating zones, where.

$T1_{Heating\ zone}$=40° C., $T2_{Heating\ zone}$=60° C., and $T3_{Heating\ zone}$=30° C.

The residence time per heating zone of the fluid bed dryer was 4 minutes each. The intermediate product obtained had a residual water content of 0.2 wt. %, and was not free-flowing. Subsequently, this intermediate was subjected to conditioning in a rotating drying drum for 3 hours and at a temperature of 60° C. The allulose crystals thus obtained had a maximum water content of 0.07 wt. %. The allulose crystals thus obtained constituted a free-flowing product.

Example 2 (According to the Invention)

Allulose crystals were obtained by centrifugation from the mother liquor from a concentrated allulose suspension (content of allulose in total dry matter of 97 wt.-%). The separated allulose crystals were subjected to temperature treatment in a continuous fluidized bed dryer for 30 minutes at a temperature of 60° C. The obtained intermediate had a residual water content of 0.2 wt.-%, and was not free-flowing. Subsequently, this intermediate was subjected to conditioning in a continuous fluid bed dryer for 3 hours and at a temperature of 60° C. The allulose crystals thus obtained had a maximum water content of 0.08 wt. %. The allulose crystals thus obtained constituted a free-flowing product.

Example 3 (According to the Invention)

Allulose crystals were obtained by centrifugation from the mother liquor from a concentrated allulose suspension (content of allulose in total dry matter of 97 wt.-%). The separated allulose crystals were subjected to temperature treatment in a vacuum dryer for 3 hours at a temperature of 30° C. and a pressure of 150 mbar. The obtained intermediate had a residual water content of 0.2 wt.-%, and was not free-flowing. Subsequently, this intermediate was subjected to conditioning in a thin-layer dryer for 24 h with air at 25°

C. with a water loading of 40% (corresponding to 8.0 g of water per kg of dry air). The allulose crystals thus obtained had a maximum water content of 0.1% by weight. The allulose crystals thus obtained constituted a free-flowing product.

Example 4 (According to the Invention)

Allulose crystals were obtained by centrifugation from the mother liquor from a concentrated allulose suspension (content of allulose in total dry matter of 97 wt.-%). The separated allulose crystals were subjected to temperature treatment in a vacuum dryer for 3 hours at a temperature of 30° C. and a pressure of 150 mbar. The obtained intermediate had a residual water content of 0.2 wt.-% and was not free-flowing. Subsequent conditioning was carried out by circulating the product by pneumatic conveying in a silo (4 hours at 60° C.). The allulose crystals thus obtained had a maximum water content of 0.001 wt.-%. The allulose crystals thus obtained represented a free-flowing product.

Evaluation of the Crystals

The solubility in water (g/liter), the increase in water content, and the sensory properties were evaluated after storage of the obtained allulose crystals in an open vessel for 24 hours by a panel consisting of five experienced and trained testers (3=pronounced, 2=present, 1=not to be determined). The results are summarized in Table 1.

TABLE 1

Solubility, sensory index and increase in water content after storage of dried crystals in an open container for 24 hours.

| Examples | Solubility index (ml) | Sensory (mean value) | Increase in water content (%) |
|---|---|---|---|
| 1 | <0.1 | 1 | <0.1 |
| 2 | <0.1 | 1 | <0.1 |
| 3 | <0.1 | 1 | <0.1 |
| 4 | <0.1 | 1 | <0.1 |
| C1 | <0.2 | 2 | >0.2 |

The experimental data show that the allulose crystals dried by the method of the invention exhibit improved results in terms of solubility and sensory properties.

Moreover, the allulose crystals dried by means of the process according to the invention, are those for which the lowest increase in water content was obtained after storage for 24 hours in an open vessel.

What is claimed is:

1. A process for drying allulose crystals comprising the following steps:
    step (a) providing non-dried allulose crystals having a water content of at most 9 weight percent and an allulose content of at least 91 weight percent;
    step (b) temperature treating the non-dried allulose crystals provided in step (a) at a temperature in the range of about 25 to about 70° C. in a drying apparatus to produce an intermediate product, wherein the temperature treatment is carried out:
        (b1) under conditions of atmospheric pressure and a residence time in the range of about 5 minutes to about 5 hours, or
        (b2) under conditions of reduced pressure below atmospheric pressure and constant temperature and a residence time ranging from about 30 min to 5 hours; and
    step (c) conditioning the intermediate product produced in step (b1) or (b2), wherein conditioning is carried out:
        (c1) under conditions of a period of about 30 min to 7 hours at a temperature in the range of about 40 to about 70° C., or
        (c2) under conditions of a period of about 15 to about 90 hours with air of a relative humidity of about 30 to about 60% and at a temperature of about 25 to about 40° C.,
    resulting in dried allulose crystals having a water content of 0.10 weight percent or less.

2. The process of claim 1, wherein the water content of the non-dried allulose crystals is at most 8 weight percent.

3. The process of claim 1, wherein the water content of the non-dried allulose crystals is at most 6 weight percent.

4. The process of claim 1, wherein the water content of the non-dried allulose crystals is 0.4 to 8 weight percent.

5. The process of claim 1, wherein the water content of the non-dried allulose crystals is 0.5 to 5 weight percent.

6. The process of claim 1, wherein the resulting dried allulose crystals are free flowing and the non-dried allulose crystals according to step (a) have a purity greater than 95% based on the total dry mass.

7. The process of claim 6, wherein the purity of the non-dried allulose crystals is greater than 98%.

8. The process of claim 6, wherein at least 98% by weight of the non-dried allulose crystals is present in the form of β-D-psicopyranose.

9. The process of claim 6, wherein
    the step (b) temperature treating tis carried out: at the (b1) conditions of atmospheric pressure and the residence time in the range of about 5 minutes to about 5 hours, and
    the step (c) conditioning is carried out: at the (c1) conditions of the period of about 30 min to 7 hours at the temperature in the range of about 40 to about 70° C.

10. The process of claim 6, wherein
    the step (b) temperature treating is carried out: at the (b1) conditions of atmospheric pressure and the residence time in the range of about 5 minutes to about 5 hours, and
    the step (c) conditioning is carried out: at the (c2) conditions of the period of about 15 to about 90 hours with air of the relative humidity of about 30 to about 60% and at the temperature of about 25 to about 40° C.

11. The process of claim 6, wherein
    the step (b) temperature treating is carried out: at the (b2) conditions of reduced pressure below atmospheric pressure and constant temperature and the residence time ranging from about 30 min to 5 hours, and
    the step (c) conditioning is carried out: at the (c1) conditions of the period of about 30 min to 7 hours at the temperature in the range of about 40 to about 70° C.

12. The process of claim 6, wherein
    the step (b) temperature treating is carried out: at the (b2) conditions of reduced pressure below atmospheric pressure and constant temperature and the residence time ranging from about 30 min to 5 hours, and
    the step (c) conditioning is carried out: at the (c2) conditions of the period of about 15 to about 90 hours with air of the relative humidity of about 30 to about 60% and at the temperature of about 25 to about 40° C.

13. A process for drying allulose crystals comprising the following steps:
- step (a) providing non-dried allulose crystals;
- step (b) temperature treating the non-dried allulose crystals provided in step (a) at a temperature in the range of about 25 to about 70° C. in a drying apparatus to produce an intermediate product, wherein the temperature treatment is carried out:
- (b1) at atmospheric pressure and a residence time in the range of about 5 minutes to about 5 hours, or (b2) under reduced pressure below atmospheric pressure and constant temperature and a residence time ranging from about 30 min to 5 hours; and
- step (c) conditioning the intermediate product produced in step (b1) or (b2), wherein conditioning is carried out:
- (c1) over a period of about 30 min to 7 hours at a temperature in the range of about 40 to about 70° C., or
- (c2) over a period of about 15 to about 90 hours with air of a relative humidity of about 30 to about 60% and at a temperature of about 25 to about 40° C.,
- resulting in a dried allulose crystals having a water content of at most 0.10 weight percent.

14. The process of claim 13, wherein the water content of the dried allulose crystals is at most 0.01 weight percent.

15. The process of claim 13, wherein the water content of the dried allulose crystals is at most 0.001 weight percent.

16. The process of claim 13, wherein the resulting dried allulose crystals are free flowing and the non-dried allulose crystals according to step (a) have a purity greater than 95% based on the total dry mass.

17. A process for drying allulose crystals comprising the following steps:
- step (a) providing non-dried allulose crystals having a water content greater than 0.5 weight percent and less than or equal to 8 weight percent, and an allulose concentration of 92 weight percent to less than 99.5 weight percent;
- step (b) temperature treating the non-dried allulose crystals provided in step (a) at a temperature in the range of about 25 to about 70° C. in a drying apparatus to produce an intermediate product having a water content of about 0.1 to about 0.5 weight percent, wherein the temperature treatment is carried out:
- (b1) at atmospheric pressure and a residence time in the range of about 5 minutes to about 5 hours, or (b2) under reduced pressure below atmospheric pressure and constant temperature and a residence time ranging from about 30 min to 5 hours; and
- step (c) conditioning the intermediate product obtained in step (b1) or (b2), wherein conditioning is carried out:
- (c1) over a period of about 30 min to 7 hours at a temperature in the range of about 40 to about 70° C., or
- (c2) over a period of about 15 to about 90 hours with air of a relative humidity of about 30 to about 60% and at a temperature of about 25 to about 40° C.,
- resulting in dried allulose crystals.

18. The process of claim 17, wherein the water content of the intermediate product is about 0.1 to about 0.3 weight percent.

19. The process of claim 17, wherein the water content of the intermediate product is about 0.15 to about 0.25 weight percent.

20. The process of claim 17, wherein the resulting dried allulose crystals are free flowing and the non-dried allulose crystals according to step (a) have a purity greater than 95% based on the total dry mass.

* * * * *